(12) United States Patent
Schwaibold et al.

(10) Patent No.: US 11,431,714 B2
(45) Date of Patent: Aug. 30, 2022

(54) METHOD OF PROVIDING SECURE COMMUNICATION IN A RESPIRATORY SYSTEM

(71) Applicant: Loewenstein Medical Technology S.A., Luxembourg (LU)

(72) Inventors: Matthias Schwaibold, Karlsruhe (DE); Igor Bychkov, Ettlingen (DE); Maria Kopaigorenko, Karlsruhe (DE); Alexander Skiba, Stutensee (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 306 days.

(21) Appl. No.: 16/537,717

(22) Filed: Aug. 12, 2019

(65) Prior Publication Data

US 2020/0053086 A1 Feb. 13, 2020

(30) Foreign Application Priority Data

Aug. 13, 2018 (DE) .......................... 102018006352.7

(51) Int. Cl.
*H04L 29/00* (2006.01)
*H04L 9/40* (2022.01)
*H04L 67/12* (2022.01)
*H04L 67/141* (2022.01)

(52) U.S. Cl.
CPC .......... *H04L 63/10* (2013.01); *H04L 63/0428* (2013.01); *H04L 63/0869* (2013.01); *H04L 67/12* (2013.01); *H04L 67/141* (2013.01)

(58) Field of Classification Search
CPC ....... H04L 63/10; H04L 67/12; H04L 67/141; H04L 63/0428; H04L 63/0869; H04L 63/08; H04L 63/04; H04L 63/12; A61M 16/022; A61M 2205/6009; A61M 2205/3553; A61M 2205/3584; A61M 2230/205; A61M 2230/10; A61M 2016/0033; A61M 2230/08; A61M 2230/14; A61M 2205/35; A61M 2016/0027; A61M 2205/8206; A61M 2205/609; A61M 2205/6018; A61M 2205/502

See application file for complete search history.

(56) References Cited

U.S. PATENT DOCUMENTS

| 7,383,339 | B1 * | 6/2008 | Meenan | H04L 12/5692 370/352 |
| 8,863,106 | B2 | 10/2014 | Schoeller | |
| 2003/0054802 | A1 | 3/2003 | Xie | |
| 2008/0271010 | A1 | 10/2008 | Schoeller | |
| 2008/0319797 | A1 * | 12/2008 | Egami | G16H 40/67 705/3 |
| 2009/0069642 | A1 * | 3/2009 | Gao | H04L 67/12 600/300 |

(Continued)

FOREIGN PATENT DOCUMENTS

EP 1705911 A1 9/2006
EP 2392253 A1 12/2011

*Primary Examiner* — Don G Zhao
(74) *Attorney, Agent, or Firm* — Abel Schillinger, LLP

(57) ABSTRACT

The invention relates to a method for secure communication in a respiratory system during the remote adjustment of a respiratory device by a server.

18 Claims, 3 Drawing Sheets

(56) References Cited

U.S. PATENT DOCUMENTS

| | | | |
|---|---|---|---|
| 2009/0191857 A1* | 7/2009 | Horn | H04W 4/70 455/419 |
| 2011/0087076 A1* | 4/2011 | Brynelsen | A61B 5/6846 600/300 |
| 2011/0093273 A1 | 4/2011 | Lee et al. | |
| 2013/0132541 A1* | 5/2013 | Falk | G06F 15/177 709/222 |
| 2013/0212378 A1* | 8/2013 | Falk | H04L 63/0272 713/155 |
| 2013/0262155 A1* | 10/2013 | Hinkamp | G06Q 10/109 705/4 |
| 2014/0206289 A1* | 7/2014 | Rahman | H04W 4/80 455/41.2 |
| 2014/0213845 A1* | 7/2014 | Bechtel | G08B 21/043 600/28 |
| 2014/0230819 A1* | 8/2014 | Rawlins | A61B 5/0022 128/204.23 |
| 2014/0280931 A1* | 9/2014 | Braun | H04L 63/10 709/225 |
| 2015/0018648 A1* | 1/2015 | Boyer | A61M 16/0051 600/323 |
| 2015/0019236 A1* | 1/2015 | Boyer | G16H 40/63 705/2 |
| 2015/0039136 A1* | 2/2015 | Gazdzinski | H04L 41/22 700/276 |
| 2015/0343160 A1* | 12/2015 | Doyle | A61M 16/0051 128/202.22 |
| 2016/0067434 A1* | 3/2016 | Schwaibold | A61M 16/0051 128/202.22 |
| 2016/0175552 A1* | 6/2016 | Harrington | A61M 16/0057 128/201.13 |
| 2016/0209062 A1* | 7/2016 | Castillo | H04L 12/2836 |
| 2017/0239433 A1* | 8/2017 | Martin | A61M 21/02 |
| 2017/0259019 A1* | 9/2017 | Cariola | A61M 16/1055 |
| 2017/0326320 A1* | 11/2017 | Baigent | A61M 16/0616 |
| 2018/0082033 A1* | 3/2018 | Meredith | A61M 16/00 |
| 2018/0164879 A1* | 6/2018 | Moffat | G06K 9/00382 |
| 2018/0182473 A1* | 6/2018 | Schwaibold | G16H 20/30 |
| 2018/0272087 A1* | 9/2018 | Von Blumenthal | G06F 21/606 |
| 2018/0294047 A1* | 10/2018 | Hosseini | G16H 15/00 |
| 2019/0156424 A1* | 5/2019 | Kimishima | G06Q 40/08 |
| 2019/0317481 A1* | 10/2019 | Glas | H04L 63/0263 |
| 2019/0327212 A1* | 10/2019 | Nakagawa | H04L 63/20 |
| 2021/0016033 A1* | 1/2021 | Boehm | H02K 5/128 |
| 2021/0113795 A1* | 4/2021 | Austin | A61M 16/0069 |
| 2021/0145308 A1* | 5/2021 | Glenn | A61M 16/0069 |
| 2021/0205558 A1* | 7/2021 | Vicario | A61B 5/4836 |

\* cited by examiner

METHOD OF PROVIDING SECURE COMMUNICATION IN A RESPIRATORY SYSTEM

CROSS-REFERENCE TO RELATED APPLICATIONS

The present application claims priority under 35 U.S.C. § 119 of German Patent Application No. 102018006352.7 filed Aug. 13, 2018, the entire disclosure of which is expressly incorporated by reference herein.

BACKGROUND OF THE INVENTION

1. Field of the Invention

The invention relates to a method for secure communication in a respiratory system during the remote setting of a respiratory device by a server, a respiratory system for carrying out the method and a respiratory device for carrying out the method.

2. Discussion of Background Information

Patent EP2392253 A1, the entire disclosure of which is incorporated by reference herein, discloses a method for updating respiratory devices, in which an operating program stored in the device is at least partly replaced by a new operating program. The described updating procedure is unspecific and not secured, however.

It would therefore be advantageous to have available a method which supports a simple and secure remote setting of the respiratory device.

SUMMARY OF THE INVENTION

The present invention provides a method for secure communication in a respiratory system for the remote setting of a respiratory device by a server, comprising
  an authentication of the respiratory device and server;
  a securing of the communication connection between the respiratory device and server;
  an encryption of the communication between the respiratory device and server;
  a verification of the integrity of the transmitted data/settings;
  a labeling of the transmitted data/settings with a time stamp and/or a device ID and/or a firmware version;
  an access protection for the server and/or testing of the access rights for the server;
  a unique assignment of a user to a respiratory device;
  a provision of a pre-selection of suitable setting options and corresponding setting parameters for an individual respiratory device by the server; and
  a testing of the suitability of the settings provided by the server by the respiratory device.

According to the invention, the confidentiality of the remote setting of a respiratory device is designed to be protected. The data should not be able to be overheard and should not be revealed to unauthorized users.

According to the invention, the integrity (of the data) during the remote setting of a respiratory device is designed to be protected. The data should not be able to be (accidentally) falsified during the communication.

According to the invention a protection against manipulation is to be ensured. For non-authorized users there will be no capability to change the settings of the respiratory device.

According to the invention the correct functioning of the respiratory device should be ensured. The new selected settings must be suitable for the device and be able to be executed thereby.

According to the invention, the transparency of the remote setting should be ensured: the users of the device and the server should be informed that a change in the settings has taken place and whether it has been carried out successfully.

The invention is characterized by the claims. The description of the embodiments complements the claims.

The invention additionally relates to a method in which a test/confirmation of the settings provided by the server is carried out by the user of the respiratory device, by the user confirming the acceptance of the settings on the respiratory device or for the respiratory device.

The invention relates alternatively or additionally to a method in which an identity of the user must be verified.

The invention relates alternatively or additionally to a method in which a confirmation/acknowledgment of the settings provided by the server is carried out by the user.

The invention relates alternatively or additionally to a method in which a deactivation of the retrieval of remote settings is carried out.

The invention relates alternatively or additionally to a method which comprises the following steps:
  establishing a communication connection between a server and a respiratory device;
  sending the current settings, which comprise at least the device type and the firmware version and/or a device ID;
  storing the current settings on the server;
  calling up the current settings on the server;
  selecting the device-specific setting options, from a database on the server, and making the device-specific setting options available;
  defining a first setting option;
  providing the first setting option for the respiratory device;
  establishing a communication connection between a server and a respiratory device;
  retrieving the new settings;
  applying the new settings;
  providing/sending a success or error message; and
  displaying a success or error message.

The invention relates alternatively or additionally to a method in which after applying the new settings of the first setting option at least one second setting option is successively defined, provided and applied.

The invention relates alternatively or additionally to a method in which the first setting option and at least one second setting option are sent to the respiratory device and applied at least partially simultaneously.

The invention relates alternatively or additionally to a method in which the communication link between the respiratory device and server terminates after sending the current settings.

The invention relates alternatively or additionally to a method in which after providing/sending a success or error message, said message is displayed on the respiratory device and on the server.

The invention relates alternatively or additionally to a method in which the communication connection between the respiratory device and server terminates after providing/sending a success or error message.

The invention relates alternatively or additionally to a method having the steps of:

establishing a communication connection between a server and a respiratory device;

sending the current settings, which comprise at least the device type and the firmware version and/or a device ID, from the respiratory device to the server;

identification of the device by the server;

selecting the device-specific setting options by the server, from a database on the server, and making the device-specific setting options available;

defining a first setting option by the server, and transmission of the first setting option by the server;

verifying the first setting option by means of the respiratory device;

confirming the first setting option by the respiratory device;

definition and transmission of the setting parameters of the first setting option by the server;

verifying the setting parameters of the first setting option by means of the respiratory device; and confirming the setting parameters of the first setting option by means of the respiratory device.

The invention relates alternatively or additionally to a method in which a review of the first setting option is carried out by the respiratory device and, if these are not suitable for the device, sending an error ID to the server and storing the error ID together with the device ID (device type and firmware version) of the respiratory device.

The invention relates alternatively or additionally to a method in which after the definition of a first setting option by the server and the transmission of the first setting option by the server, at least one second setting option is defined and transmitted.

The invention relates alternatively or additionally to a method in which a review of the first setting option is carried out by the respiratory device and, if these are not suitable for the device, sending a confirmation ID to the server together with the accepted values of the first setting option, and storing the confirmation ID together with the device ID (device type and firmware version) of the respiratory device.

The invention relates alternatively or additionally to a method in which the modified setting is signaled to the user of the respiratory device on the display of the respiratory device and/or on a personal communication device of the user.

The invention relates alternatively or additionally to a method in which the personal communication device is a hand-held computer device such as a tablet, a mobile phone, a telephone, a smartphone, a personal digital assistant (PDA), a desktop computer, a laptop computer and the like.

The invention relates alternatively or additionally to a method in which an administrator enters a message text for the user on the server and this message text is transmitted from the server to the respiratory device and appears on the display there, or is transmitted from the server to a user's personal communication device.

The invention relates alternatively or additionally to a method in which an administrator receives a reply message from the server on the display, as to whether and when the new settings have been accepted by the respiratory device, or if an error occurred.

The invention relates alternatively or additionally to a method in which an administrator must be authenticated on the server before submitting new settings for the respiratory device.

The invention relates alternatively or additionally to a method in which an administrator must be authenticated on the server before receiving new settings for the respiratory device.

The invention relates alternatively or additionally to a method in which a user must confirm the receipt of new settings for the respiratory device.

The invention relates alternatively or additionally to a method in which the communication with the server can be deactivated.

The invention relates alternatively or additionally to a method in which accessory settings, such as a different hose type, for the respiratory device, are changed and activated by the server.

The invention also relates to a system which is designed and configured for executing the method according to at least one of the preceding aspects.

The invention also relates to a respiratory device which is designed and configured for executing the method according to at least one of the preceding aspects.

The invention also relates to a server which is designed and configured for executing the method according to at least one of the preceding aspects.

In the establishment of a communication connection between a server and the respiratory device an authentication of the device and the server takes place.

For authentication and encryption, certificates (private/public) can also generally be used, which are stored in the respiratory device, for example, (because they have already been stored in a memory of the device during manufacture or subsequently) and which are verified for their validity during the communication between the server and the device with a database via a separate communication channel.

As soon as a communication connection is established, the communication connection is secured.

According to the invention it is also provided that the communication via the communication connection is encrypted.

During the communication a verification of the integrity of the data is also carried out. The data should not be able to be (accidentally) falsified in the communication, for example, due to poor data quality.

During the communication the data are also marked with a time stamp and/or a device ID and firmware version. For example, a marking can be carried out by addition of at least one time stamp (for example, for activation and reception), in order to determine the chronological sequence of the applied settings and to be able to identify the most recent known setting, even when using asynchronous data processing.

According to the invention, an access protection for the server and verification of the access rights for each administrator are also provided.

According to the invention a unique assignment of a user to a respiratory device is also provided.

According to the invention it is also provided that the server for the specific respiratory device offers a specific pre-selection of suitable setting options and appropriate setting parameters from a plurality of setting options and setting parameters. This facilitates the specification of the setting options and setting parameters and prevents the specification of nonsensical combinations. The pre-selection of suitable setting options and appropriate setting parameters is achieved by the fact that the server identifies the respiratory device based on its device ID and/or the device type and/or the serial number and/or the firmware version.

According to the invention a further verification of the suitability of the settings provided by the server can be carried out by the respiratory device.

According to the invention a further verification of the settings provided by the server can be carried out by the user. This verification is provided as an additional security measure and stipulates that the user confirms the acceptance of the settings on the respiratory device or for the respiratory device.

According to the invention, a verification of the suitability of the settings provided by the server can be carried out by requiring the user's identity to be verified.

According to the invention a confirmation/acknowledgment of the settings provided by the server can be carried out by the user.

According to the invention, an option to deactivate the retrieval of remote settings can be provided. As a result, at least in the event of deactivation an additional protection against remote setting of the respiratory device can be carried out.

DETAILED DESCRIPTION OF EXEMPLARY EMBODIMENTS OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
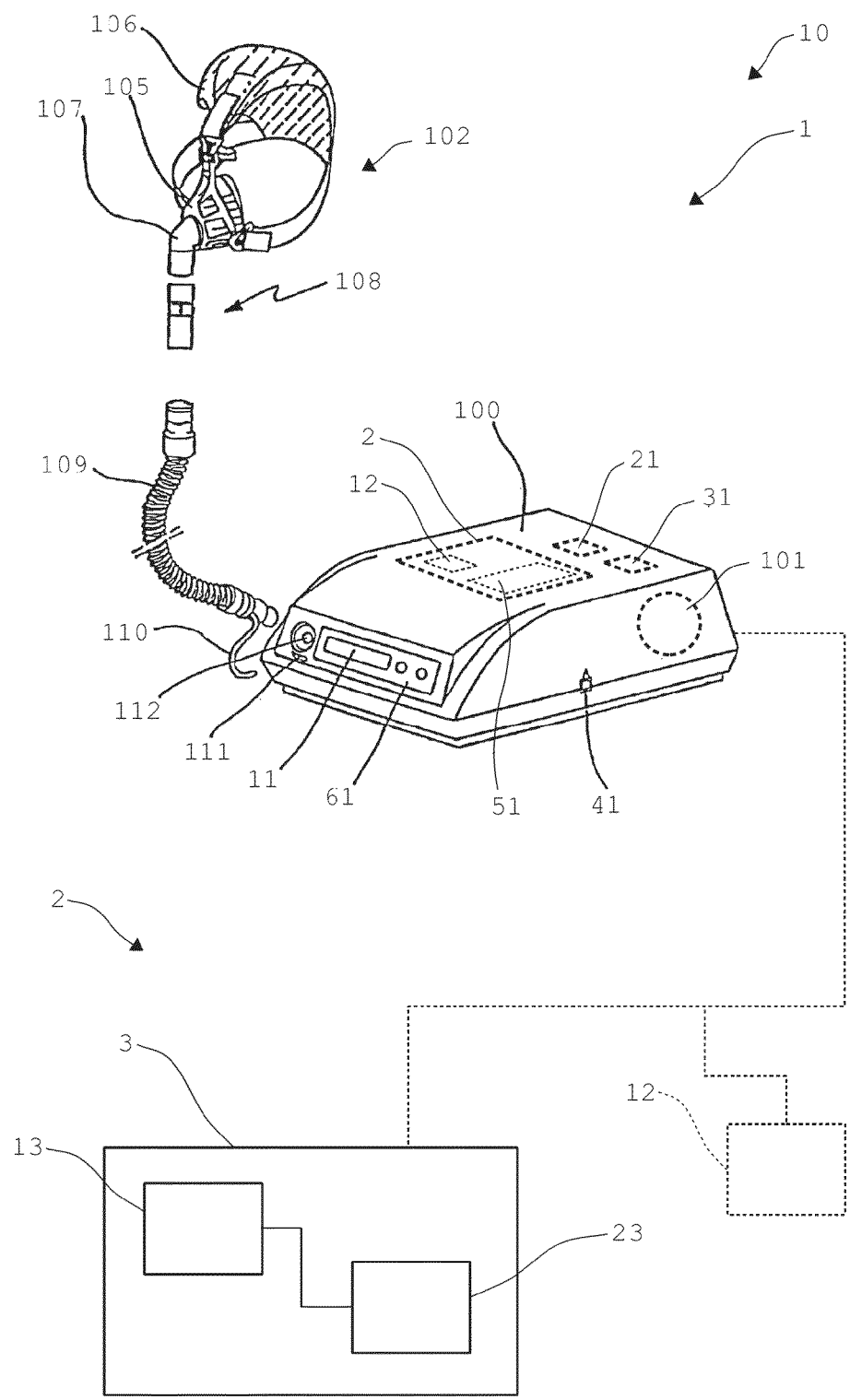
FIG. 1 a highly schematic representation of a respiratory system according to the invention.

FIG. 1 shows a respiratory system 10 according to the invention, which here comprises a respiratory device 1 used as a home respiratory device 11 or sleep therapy device. The respiratory device 1 can also be implemented as a clinical respirator, CPAP or APAP, cough treatment device or high-flow device 1. The respiratory device can also have at least one mode for (nasal) high-flow therapy or high-flow oxygen therapy, which can be selected and parameterized by the remote setting. The respiratory device 1 is suitable and designed for implementing the method according to the invention.

The respiratory device 1 comprises a respiratory apparatus 100, which is embodied as a blowing device and/or valve device 101, for example, for producing an air flow for respiration. To control the respiratory apparatus 100 and to collect therapy data, a monitoring device 21 is provided. The operation and adjustment of the respiratory device 1 are carried out via a user interface 61 with operating controls 103 and a display device 11.

The respiratory device 1 has a respiration interface 102 to supply the air flow to a user for breathing. The respiration interface 102 shown here is a breathing mask 105 designed as a nasal mask. To fix the breathing mask 105 in place, a helmet 106 is provided. The respiration interface 102 may also be designed, for example, as a full-face mask, as a nasal pillow, a tube or a laryngeal mask.

To connect the respiration interface 102 to the respiratory apparatus 100 a connecting hose 109 is provided, which is connected to the respiratory apparatus 100 by means of a coupling device 112. By way of a coupling element 107, the connection hose 109 is connected to the respiration interface 102. Between the connecting hose 109 and the coupling element 107 an exhalation element 108 is arranged, which comprises a valve or is implemented as such. The exhalation element 108 is provided, in particular, to prevent the user breathing back into the respiratory device 1 while exhaling.

The monitoring device 21 here is operatively connected to a sensor device, not shown in detail here, which has one or more sensors for recording device parameters and/or patient parameters and/or other characteristic variables for respiration.

For example, the monitoring device 21 comprises a pressure sensor, not shown in detail here, which detects the pressure ratios with respect to the respiration interface 102. To this end, the pressure sensor is connected to the respiration interface 102 via a pressure measuring hose 110. The pressure measuring hose 110 is connected to the monitoring device 21 via an input nozzle 111.

Furthermore, the monitoring device 21 here is used to control the respiratory apparatus 100. The monitoring device 21 provides a necessary minimum pressure and compensates for pressure fluctuations caused by the breathing activity of the user. For example, the monitoring device 21 also detects the current pressure in the breathing mask 105 and adjusts the performance of the respiratory apparatus 100 accordingly, until a desired respiratory pressure is present.

The device parameters required to adjust the respiratory apparatus 100 and the device configuration and/or device software are stored in a memory device 31.

The monitoring device 21 can also be designed to record patient parameters. To do so, the monitoring device 21 can be equipped with sensors for measuring the respiratory excursion, for measuring oxygen saturation of the blood and/or for measuring an EEG, EMG, EOG or ECG activity.

For example, the monitoring device 21 carries out a regulation to target device parameters, which have been individually calculated and specified in advance on the basis of the characteristic breathing of a user.

It is also possible that the respiratory apparatus 100 is adjusted dynamically, in particular depending on the respiratory phase of the user. For example, by means of the monitoring device 21 a respiratory phase change can be detected, so that a higher or lower pressure can be provided depending on the respiratory phase. For example, the respiratory device 1 can be designed as a CPAP or APAP device. The respiratory device 1 can also be designed as a bilevel device. For example, the respiratory device 1 reacts to specific respiratory events, such as snoring, periods of shallow breathing and/or obstructive pressure peaks, with appropriate settings of the device parameters.

The pressure ratios recorded by the monitoring device 21 are stored together with additional device parameters in a memory device 31. In addition, the pressure ratios set by the monitoring device 21 and/or the pressure adjustments performed are also stored as device parameters in the memory device 31. The patient parameters can also be stored in the memory device 31. In addition, data on compliance and mask leak-proofing may be stored.

Examples of device parameters that can be stored are a starting therapy pressure, a maximum therapy pressure, a minimal therapy pressure and/or a target volume and/or other suitable device parameters for adjusting the respiratory apparatus 100. These device parameters are retrieved from the memory device 31 by the monitoring device 21 to adjust the respiratory apparatus 100.

Furthermore, the pressure ratios recorded over the therapy period and/or other device parameters and/or patient parameters recorded in the context of therapeutic profiles are stored in the memory device 31. Examples of therapy profiles that can be registered are a flow profile, a pressure profile and/or an event history. The therapy profiles are provided to the memory device 31 by the monitoring device 21, which records these data during the therapy.

The device parameters and/or patient parameters and/or therapy profiles stored in the memory device 31 are retrieved and evaluated to provide one or more therapy statistics. The therapy statistics are stored in the memory device 31. In doing so, for example, an average pressure and/or the duration of treatment and/or a leakage parameter can be determined and stored.

To be able to submit the therapy data to a therapeutic or diagnostic analysis or to monitor and/or adjust the operation of the respiratory device 1, a transmission of the therapy data or settings or a device ID to at least one server 3 by means of a data processing device 2 is provided. The data processing device 2 here provides the components or software so that the server 3 can interpret the data from the respiratory device 1 and vice versa.

The respiratory system 10 can also comprise two or more servers 3, which are connected to one or more respiratory devices 1.

The transmission is carried out by means of a transmission device 51 by wireless and/or wired means. The transmission device 51 can be a part of the respiratory device, or assigned to the respiratory device as a separate component. The respiratory device can be connected to a modem 12, as a transmission device 51, or comprise a modem 12.

The transmission can take place over one or more cable interfaces such as USB, serial, LAN, databus, etc. The transmission may also take place over one or more wireless interfaces, for example mobile radio, LPWAN, Bluetooth, infrared, Sigfox, Lora etc.

The server 3 can comprise at least one server 13 and/or at least one personal computer (PC) 23 or else be implemented as a cloud computer. Thus, for example, from a PC 23 a web server 13 can be accessed, which in turn is connected via a network connection to one or more respiratory devices 1.

In addition, the therapy data can also be stored at least partially on a portable storage medium 41. The storage medium 41 is implemented, for example, as a memory card or a hard disk or a USB mass storage device. The storage medium 41 can be removed from the device and read using a reader and, for example, a computer, tablet, or smartphone.

The therapy data or other data can also be read out via a display 11 located in the device 1 and/or connected to the device 1, or a user interface 61.

Using these same interfaces, the device 1 can be equipped with new configuration data or new program code or functions in the device 1 can be activated. One or more data memories 31, 41 in the device 1 are thus preferably written to and/or read externally.

From the server 3, the therapy data can be accessed from a remote location so that a location-independent evaluation is possible. Thus, administrators (doctors, health providers, etc.) can access the data in the respiratory system 10. For data protection and data security reasons, access is restricted to the devices 1 used by themselves, for example. The patient (user) receives access only to his/her device 1, for example. Professionals such as providers and physicians (administrators) receive access, for example, to the devices 1 of all their patients.

Figure 2:
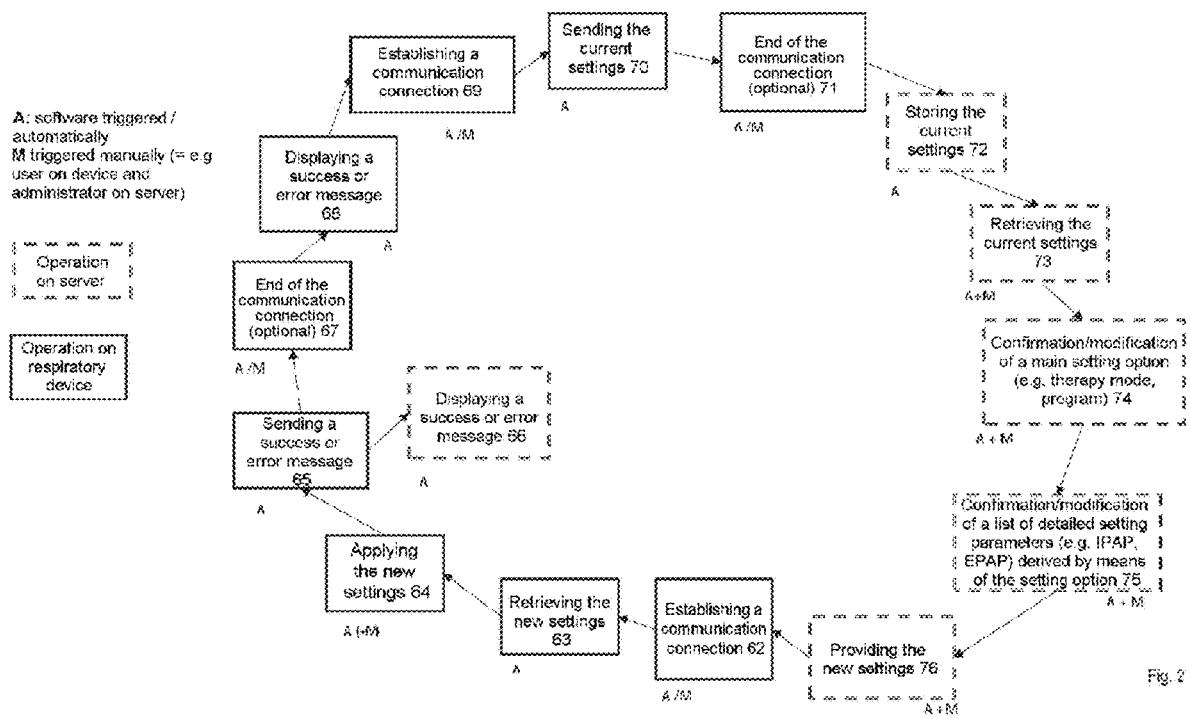
FIG. 2 an example of a communication sequence between a respiratory device and a server.

FIG. 2 shows an example of a communication sequence between the respiratory device 1 and the server 3.

The establishment of a communication connection between a server and the respiratory device 69 is initiated, for example, by the respiratory device (or the server 3) automatically, or manually by a user (patient or administrator). For example, the connection is established automatically in a preset or adjustable time interval, such as every 5 or 60 minutes. As soon as the communication connection is established, the current settings of the respiratory device are sent automatically to the server 3, wherein the settings comprise, for example, at least the device type and the firmware version and/or a device ID 70. Optionally, after sending the current settings 70 the communication link between the respiratory device and server 3 can terminate 71. This process can be initiated automatically or by a user.

Storage of the current settings on the server 72 takes place automatically.

Initiated automatically and/or manually by a user, the current settings are then retrieved on the server 73.

Initiated automatically and/or manually by a user, a selection of device-specific setting options is then made from a database on the server, and the device-specific setting options 74 are made available. Optionally, these can also be confirmed or amended.

Initiated automatically and/or manually by a user, the device-specific setting parameters for the setting options 75 are then selected.

Initiated automatically and/or manually by a user, the new setting for the respiratory device 76 is then provided.

Initiated automatically or manually by a user, a communication connection is then established between the server and the respiratory device 62.

The new settings 63 are then automatically retrieved by the respiratory device.

Initiated automatically and/or optionally manually by a user, the new settings 64 are then applied. A success or error message 65 is then automatically sent.

The display of a success or error message 68 takes place automatically. This can be optionally or additionally displayed on the respiratory device and/or the server (66, 68).

The success or error message can also be sent as a notification, for example in the form of an e-mail, SMS, or Whatsapp message to a communication device of the user and/or administrator.

The settings which the server sends to the respiratory device can also be, in addition to the respiratory settings, a selection of text/voice blocks that the respiratory device or at least a human-machine interface connected thereto should output to its user, in particular messages or questions. The questions relate preferably to the symptoms of the disease, the side effects of the respiratory therapy, the patient's quality of life or health condition, or error conditions of the respiratory device. The text/voice blocks can be stored in the device and activated by the remote setting, or else they are sent to the respiratory device by the remote setting itself.

The settings are usually respiratory settings, or any instruction that causes a change in status on the device, such as comfort settings, device settings (display brightness, . . . ), alarm settings, data settings, or else actions. The setting options are then, for example, respiration pressures, respiratory rate, volume or peak inspiration pressure, peak expiratory pressure, backup frequency, a text message for the device display, reboot the device, output audible signal, change over respiratory program, update firmware.

The associated setting parameters 75 are then, for example, the pressure values or specific frequencies or other specific values or texts or characters that can be entered freely (for communication).

Applicable settings, in addition to the permanently effective settings such as firmware code, respiration mode, respiration pressures, respiration rate, comfort parameters, are also actions that can be triggered by remote settings on the device at least once, for example restarting the device
sending specific data from the device memory
deleting specific data in the device memory
sending an authentication
carrying out at least one self-test of the device
carrying out at least one action to clean the device or its accessories
carrying out at least one respiration maneuver, for example the start or ending of respiration, application of a different pressure from the value normally set for a limited period of time
displaying a specific piece of information graphically, visually or acoustically in the device One application case of the remote setting which is also provided according to the invention is an update of the respiratory device with new software or firmware. The server can send such updates to the respiratory device automatically or at the initiative of the administrator.

On the server different administrators can have different rights to modify device settings. According to the invention a user rights management of the server is provided, for setting/adjusting user rights. So, for example, the user of the respiratory device itself could also be an administrator of the server and/or only be allowed to perform a limited set of settings (for example, comfort parameters). Or a particular (technical) administrator may also only change a limited number of settings. This is controlled by the user rights management of the server or can be specified thereby.

In this method of the remote setting described, accessory components that are connected to the respiratory device can also be set remotely. In particular, humidifiers, hose heater, sensor modules (SpO2, FiO2, CO2), alarm modules, (re-chargeable) battery modules, oxygen concentrators, oxygen/gas mixers.

Depending on the selected setting for at least one (main) parameter, it is possible for the server to offer or suggest dynamically to the administrator more or fewer additional secondary setting parameters. For example, when selecting an automatic pressure system (APAP, auto-EPAP, target volume) a lower and an upper pressure limit are preset or suggested. For example, on switching off the automatic pressure system a fixed pressure value, or lower and upper pressure limit, is preset or proposed. For example, when selecting a target volume, a lower and an upper pressure limit are preset or proposed. For example, on selecting a frequency a lower and an upper pressure limit are preset or proposed. For this purpose the associated setting logic of the respiratory device is mirrored on the server, for example, in such a way that these adjustments of the provided secondary parameters are carried out without the server needing to communicate with the respiratory device after the choice of the main setting parameter and requesting from this the list of secondary setting parameters.

Depending on the selected setting for at least one setting option, it is possible for the server to offer or suggest to the administrator more or fewer additional "sensible" setting options dynamically. For example, on shutting down the automatic pressure system a safety frequency is preset or proposed. For example, on selecting a frequency a lower and an upper pressure limit are preset or proposed. For this purpose the associated setting logic of the respiratory device is mirrored on the server, for example, in such a way that these adjustments of the provided secondary parameters are carried out without the server needing to communicate with the respiratory device after the choice of the main setting parameter and requesting from this the list of secondary setting parameters.

The method optionally or additionally provides that the communication link between the respiratory device and server 3 terminates 67 after providing/sending a success or error message 65. The termination 67 of the communication connection can be initiated automatically, or optionally manually by a user.

Figure 3:
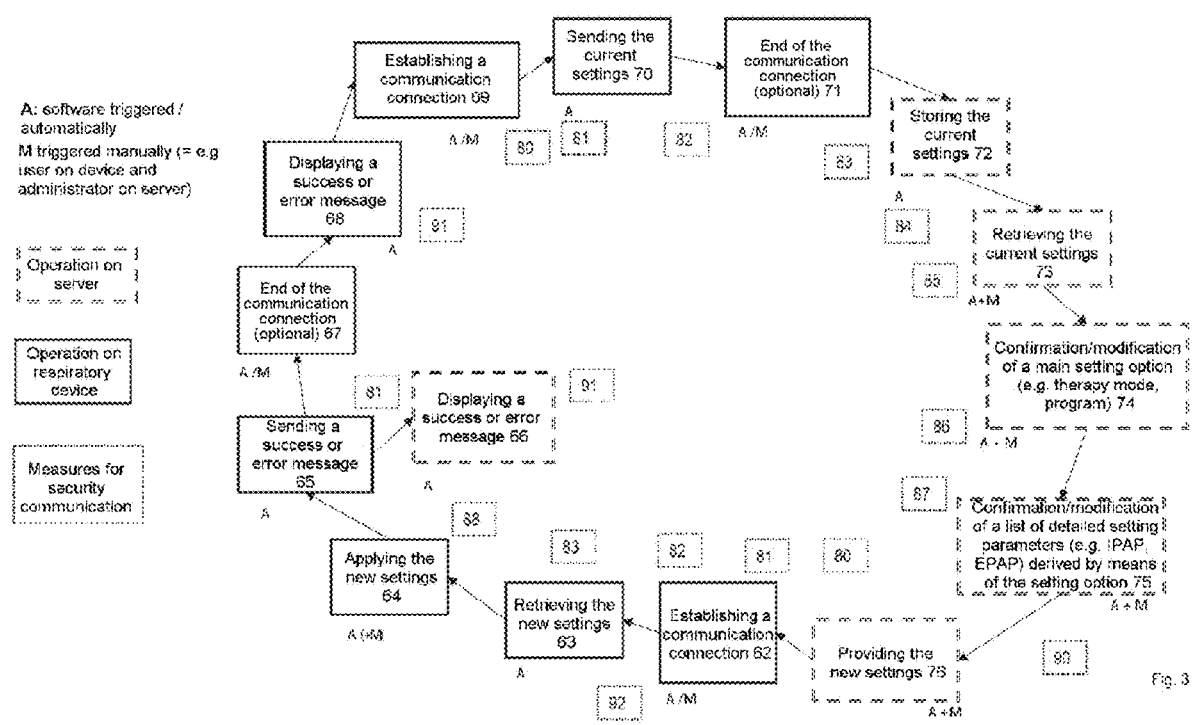
FIG. 3 an example of the security mechanisms that are implemented during a communication sequence between the respiratory device and the server.

FIG. 3 shows examples of the security mechanisms that are implemented during a communication sequence between the respiratory device 1 and the server 3.

During the establishment of a communication connection between a server and the respiratory device 69 an authentication of the device and the server 80 takes place. For example, authentication can be carried out by verifying a device type and serial number, or a device ID. The authentication can alternatively or additionally be carried out by verifying the SIM card number (for example, if a SIM card is used in a modem). The authentication can alternatively or additionally be carried out by verifying the IP address of the server. The authentication can alternatively or additionally be carried out by a mutual verification of public and/or private certificates between respiratory device and server. The authentication can alternatively or additionally be carried out by verifying a security ID code of the device. The authentication can alternatively or additionally be carried out by communication from the respiratory device only being possible with a defined access point (APN). The authentication can alternatively or additionally be carried out by requiring a specific, defined question-and-answer sequence to be followed between the device and the server. The authentication can alternatively or additionally be carried out by requiring a verification of the combination of IDs/serial numbers of a plurality of hardware components of the device.

As soon as a communication connection is established, the communication connection 81 is secured. The communication connection 81 can be secured, for example, by using a specific, defined access point (private APN). The communication connection 81 may alternatively or additionally be secured by implementing an end-to-end encryption between the respiratory device and the server. The communication connection 81 may alternatively or additionally be secured by a VPN channel (virtual private closed-loop communication network) being set up from the defined access point (APN) to the server.

The communication connection 81 may alternatively or additionally be implemented in such a way that a firewall is established. The communication connection 81 may alternatively or additionally be implemented in such a way that unnecessary communication facilities and ports are blocked.

According to the invention it is also provided that the communication via the communication connection is encrypted 82. The encryption 82 can be implemented, for example, by using a TLS or SSL standard or variants thereof. The encryption 82 may alternatively or additionally be implemented by using a direct encryption using a key whose length is greater than or equal to 8 bits. The encryption 82 can alternatively or additionally be implemented by applying HTTPS or SFTP or variants thereof.

During the communication a verification of the integrity of the data is also carried out. The data should not be able to be (accidentally) falsified in the communication, for example, due to poor data quality.

The integrity 83 can be verified, for example, by appending a checksum to the message. The integrity 83 can alternatively or additionally be verified by the use of transmission protocols with a data verification, for example http, MQTT, TCP/IP, GSM, Bluetooth. The integrity 83 can alternatively or additionally be verified by addition of a hash code to the message, wherein the hash code is calculated from the content of the message and a pre-defined security key. The integrity 83 can alternatively or additionally be verified by addition of a hash code to the message, wherein the code is calculated from the content of the message and a pre-defined security key and a random component.

During the communication the data are also marked 84 with a time stamp and/or a device ID and firmware version. For example, a marking 84 can be carried out by addition of at least one time stamp (for example, for activation and reception), in order to determine the chronological sequence of the applied settings and to be able to identify the most recent known setting, even when using asynchronous data processing. A marking 84 can be carried out, for example, by marking the stored settings with device type and firmware version, so that the server in case of a later change of the settings can only propose (to the user) appropriate setting options.

According to the invention, an access protection for the server 3 and a verification of the access rights for each administrator are also provided 85. The access protection for the server 85 can alternatively or additionally be carried out by

- a physical protection of the server against unauthorized manipulation being present;
- an encrypted data connection existing between the browser/frontend and the server for authorized administrators;
- access to the server only being allowed for authorized administrators, depending on their individual user rights;
- a protection against electronic access to the server being provided through a firewall or security container, or a data separation;
- a protection against electronic access to the server via the browser/the frontend is prevented, for example, by measures such as a rights escalation or cross-site scripting or OWASP Top 10 threats;
- a strong authentication of the administrators on the server takes place, for example, with 2-factor authentication or by biometric verification (fingerprint, iris scan, . . . ).

According to the invention a unique assignment 86 of a user to a respiratory device is also provided.

The unique assignment 86 is ensured, for example, by an assignment of a device to a user via its serial number or device ID. The unique assignment 86 is alternatively or additionally ensured by confirmation procedures during the assignment, for example, by sending an identifier between the device and the server or a manual confirmation on the device. The unique assignment 86 is alternatively or additionally indicated (for the administrator) and thus monitored by a display of user-name or ID and device serial number or device ID during the entire setting process. The unique assignment 86 is alternatively or additionally supported by a communication/a prompt (to the administrator) to verify the serial number of the device on each setting operation, for example, including when settings are made with an independent source, such as an ERP system. The unique assignment 86 is alternatively or additionally ensured by a communication (a call) with the device user during the adjustment process. This includes requesting the confirmation message. The unique assignment 86 is alternatively or additionally ensured by a communication with the device user, by the latter being prompted to carry out a manual input or output of a confirmation code on the device, notified by telephone for example, to activate the modified settings.

According to the invention it is also provided that the server for the specific respiratory device offers 87 a specific pre-selection of suitable setting options 74 and appropriate setting parameters 75 from a plurality of setting options and setting parameters. This facilitates the specification of the setting options and setting parameters and prevents the specification of nonsensical combinations. The pre-selection of suitable setting options and appropriate setting parameters 87 is achieved by the fact that the server identifies the respiratory device based on its device ID and/or the device type and/or the serial number and/or the firmware version. From a database the server then identifies only those setting options and setting parameters that are compatible with the individual respiratory device. The pre-selection of suitable setting options and matching setting parameters 87 is alternatively or additionally achieved by the fact that after changing each setting value (setting options and/or setting parameters) or at least before the confirmation of the whole of the new settings, a check is made to ensure that all dependencies between the setting values have been complied with or are consistent. For example, a plausibility check is made of an upper limit of pressure ranges relative to the lower limits of pressure ranges. The pre-selection of suitable setting options and appropriate setting parameters 87 is alternatively or additionally achieved by an automatic adjustment of dependent setting values. The pre-selection of suitable setting options and appropriate setting parameters 87 is alternatively or additionally achieved by the fact that the server identifies the respiratory device based on its device ID and/or the device type and/or the serial number and/or the firmware version and also the user of the device (for example, using a user/respiratory device mapping that is accessible for the server), and on the basis of stored user information and stored respiratory device information the server automatically only offers or applies such setting options and/or setting parameters as are suitable for the individual combination of user/respiratory device. In this case, the suitability can be stored such that it is accessible to the server.

According to the invention a further verification of the suitability 88 of the settings provided by the server can be carried out by the respiratory device. This verification is provided as an additional security measure, since changes may have occurred between sending the latest settings and fetching the new settings (for example, the FW version may have changed or else a new respiratory device may have been supplied to the same patient).

According to the invention a further verification of the settings provided by the server can be carried out by the user. This verification is provided as an additional security measure and stipulates that the user confirms 89 the acceptance of the settings on the respiratory device or for the respiratory device. The confirmation of the acceptance 89 may also be carried out by the user pressing a confirmation button on the device or confirming acceptance acoustically. The confirmation of the acceptance 89 can also be carried out in such a way that the user must enter a security code on the device or must communicate a code to the administrator. This code can be available to the user permanently or newly communicated for each change in the settings, for example, in the form of an e-mail, SMS, Whatsapp message to a communication device of the user and/or the respiratory device.

According to the invention, a verification of the suitability of the settings provided by the server can be carried out by requiring the user's identity to be verified 90. The identity 90 can be verified at the moment of the provision of new settings. The identity 90 can be verified by requiring a password or one-time password or security code to be communicated or entered. The identity 90 can be verified by a biometric verification (for example, fingerprint, iris scan, voice verification).

According to the invention a confirmation/acknowledgment 91 of the settings provided by the server can be carried out by the user. The acknowledgment 91 by users is used to ensure the viewing of a message about the planned or implemented changes and will only then enable the latter. The acknowledgment 91 by users can be carried out by a mouse click or keystroke or a gesture or touch input or consent by voice.

According to the invention, an option to deactivate the retrieval of remote settings 92 can be provided. As a result, at least in the event of deactivation an additional protection against remote setting of the respiratory device can be provided. The deactivation 92 can be activated directly on the device as a setting option. The deactivation can comprise only the sending of current settings or the sending/retrieval of settings. In this case the retrieval may not take place for each sending operation, but only for certain operations, for example initiated manually or in a time-controlled manner.

What is claimed is:

1. A method for secure communication in a respiratory system for a remote setting of a respiratory device by a server, wherein the method comprises:
   authenticating the respiratory device and the server;
   securing the communication connection between the respiratory device and the server;
   encrypting the communication between the respiratory device and the server;
   verifying an integrity of transmitted data/settings;
   labeling the transmitted data/settings with a time stamp and/or a device ID and/or a firmware version;
   providing an access protection for the server and/or testing of access rights for the server;
   providing a unique assignment of a user to the respiratory device;
   providing a pre-selection of suitable setting options and matching setting parameters for the respiratory device by the server; and
   checking a suitability of the setting options provided by the server by the respiratory device;
   the server identifying from a database only those setting options that have matching setting parameters which are compatible with the respiratory device.

2. The method of claim 1, wherein a check/confirmation of the setting options provided by the server is carried out by a user of the respiratory device, by the user confirming acceptance of the setting options on the respiratory device or for the respiratory device.

3. The method of claim 1, wherein an identity of the user is verified.

4. The method of claim 1, wherein a confirmation/acknowledgment of the setting options provided by the server is carried out by the user.

5. The method of claim 1, wherein a deactivation of a retrieval of remote settings is carried out.

6. The method of claim 1, wherein the method comprises:
   establishing a communication connection between the server and the respiratory device;
   sending current settings, which comprise at least device type and firmware version and/or device ID;
   storing the current settings on the server;
   calling up the current settings on the server;
   selecting device-specific setting options, from a database on the server, and making the device-specific setting options available;
   defining a first setting option;
   providing the first setting option for the respiratory device;
   establishing a communication connection between the server and the respiratory device;
   retrieving new settings of the first setting option;
   applying the new settings of the first setting option;
   providing/sending a success or error message; and
   displaying a success or error message.

7. The method of claim 6, wherein after applying the new settings of the first setting option at least one second setting option is successively defined, provided and applied.

8. The method of claim 7, wherein the first setting option and the at least one second setting option are sent to the respiratory device and applied at least partly simultaneously.

9. The method of claim 6, wherein after providing/sending a success or error message, said message is displayed on the respiratory device and the server.

10. The method of claim 1, wherein the method further comprises:
    establishing a communication connection between the server and the respiratory device;
    sending current settings, which comprise at least device type and firmware version and/or a device ID, from the respiratory device to the server;
    identification of the respiratory device by the server;
    selecting device-specific setting options by the server, from a database on the server, and making the device-specific setting options available;
    defining a first setting option by the server, and transmission of the first setting option by the server;
    reviewing the first setting option by the respiratory device;
    confirming the first setting option by the respiratory device;
    defining and transmission of setting parameters of the first setting option by the server;
    verifying the setting parameters of the first setting option by the respiratory device; and
    confirming the setting parameters of the first setting option by the respiratory device.

11. The method of claim 10, wherein a review of the first setting option is carried out by the respiratory device and if this is not suitable for the respiratory device, an error ID is sent to the server and the error ID is stored together with the device ID (respiratory device type and firmware version) of the respiratory device.

12. The method of claim 10, wherein after definition of a first setting option by the server and transmission of the first setting option by the server, at least one second setting option is defined and transmitted.

13. The method of claim 10, wherein a review of the first setting option is carried out by the respiratory device and, if this is not suitable for the respiratory device, a confirmation ID is sent to the server together with the accepted values of the first setting option, and the confirmation ID is stored together with the device ID (respiratory device type and firmware version) of the respiratory device.

14. The method of claim 13, wherein a modified setting is signaled to the user of the respiratory device on the display of the respiratory device and/or on a personal communication device of the user.

15. The method of claim 1, wherein an administrator enters a message text for the user on the server and this message text is transmitted from the server to the respiratory device and appears on the display there or is transmitted from the server to a user's personal communication device.

16. The method of claim 15, wherein an administrator receives a reply message from the server on the display, as to whether and when new settings have been accepted by the respiratory device or if an error occurred.

17. A method for secure communication in a respiratory system for a remote setting of a respiratory device by a server, wherein the method comprises:
   authenticating the respiratory device and the server;
   securing the communication connection between the respiratory device and the server;
   encrypting the communication between the respiratory device and the server;
   verifying an integrity of transmitted data/settings;
   labeling the transmitted data/settings with a time stamp and/or a device ID and/or a firmware version;
   providing an access protection for the server and/or testing of access rights for the server;
   providing a unique assignment of a user to the respiratory device;
   providing a pre-selection of suitable setting options and matching setting parameters for the respiratory device by the server; and
   checking a suitability of the setting options provided by the server by the respiratory device;
and further comprises:
   establishing a communication connection between the server and the respiratory device;
   sending current settings, which comprise at least device type and firmware version and/or a device ID, from the respiratory device to the server;
   identification of the respiratory device by the server;
   selecting device-specific setting options by the server, from a database on the server, and making the device-specific setting options available;
   defining a first setting option by the server, and transmission of the first setting option by the server;
   reviewing the first setting option by the respiratory device;
   confirming the first setting option by the respiratory device;
   defining and transmission of setting parameters of the first setting option by the server;
   verifying the setting parameters of the first setting option by the respiratory device; and
   confirming the setting parameters of the first setting option by the respiratory device;
   and wherein a review of the first setting option is carried out by the respiratory device and, if this is not suitable for the respiratory device, a confirmation ID is sent to the server together with the accepted values of the first setting option, and the confirmation ID is stored together with the device ID (respiratory device type and firmware version) of the respiratory device.

18. The method of claim 17, wherein a modified setting is signaled to the user of the respiratory device on the display of the respiratory device and/or on a personal communication device of the user.

* * * * *